United States Patent [19]
Ochoa et al.

[11] Patent Number: 6,139,584
[45] Date of Patent: Oct. 31, 2000

[54] PROXIMAL FEMORAL SLEEVE FOR A REVISION HIP PROSTHESIS

[75] Inventors: Jorge A. Ochoa, Norton; Farid Bruce Khalili, Chestnut Hill, both of Mass.

[73] Assignee: Depuy Orthopaedics, Inc., Warsaw, Ind.

[21] Appl. No.: 09/219,583

[22] Filed: Dec. 22, 1998

[51] Int. Cl.⁷ ........................................ A61F 2/36
[52] U.S. Cl. ........................................ 623/23.46
[58] Field of Search .................. 623/23, 20, 18, 623/23.11, 23.18, 23.21, 23.23, 23.46, 20.15, 20.2, 18.11

[56] References Cited

U.S. PATENT DOCUMENTS

| | | | |
|---|---|---|---|
| 5,858,020 | 1/1999 | Johnson et al. | 623/23 |
| 5,906,644 | 5/1999 | Powell | 623/23 |

Primary Examiner—V. Miller
Assistant Examiner—Alvin Stewart
Attorney, Agent, or Firm—Nutter, McClennen & Fish, LLP

[57] ABSTRACT

A sleeve component for engagement with a prosthetic component, such as a revision femoral component, compensates for bone loss and/or anatomical anomalies. In one embodiment, the sleeve includes a compensating region which provides an eccentric outer surface for offsetting proximal, posterior bone loss in the patient's femur. The sleeve has a bore through which the stem of a femoral component is insertable. The inner walls of the bore taper so as to complement a proximal outer surface of the stem when the sleeve abuts a shoulder portion of the femoral component. In one embodiment, the compensating region is defined by a radius which is offset from the longitudinal axis of the sleeve. In another embodiment, the compensating region is defined by a radius extending from the longitudinal axis and having an increased length.

21 Claims, 7 Drawing Sheets

PROXIMAL FEMORAL SLEEVE FOR A REVISION HIP PROSTHESIS

FIELD OF THE INVENTION

The present invention relates to prosthetic components, and more particularly, to sleeve components adapted for use with implantable prosthetic components.

BACKGROUND OF THE INVENTION

Joint arthroplasty is a well known surgical procedure by which a diseased and/or damaged natural joint is replaced by a prosthetic joint. Joint arthroplasty is commonly performed for hips, knees, elbows, and other joints. A hip arthroplasty includes the insertion of a prosthetic femoral stem component into the medullary canal of the femur. A ball or head is affixed to an end of the stem for articulation within a natural acetabulum or prosthetic acetabular component in the case of a total hip arthroplasty.

It is important that the femoral stem be securely positioned within the femur so as to achieve adequate initial fixation, as well to promote long term stability of the implant. Femoral components can have various design characteristics to provide optimal fixation properties, such as surface features for encouraging bony ingrowth, tailored flexibilities for reducing stress shielding, and particular surface properties for maximizing or minimizing adhesion to cement. While such femoral components may extend the useful life of the implant, a surgical revision of the prosthesis may become necessary after an extended period of time.

One problem associated with the revision of a femoral component is the difficulty of implanting a revision femoral component along the same longitudinal axis as the primary or original implant. It is desirable to implant the revision femoral component along the primary axis to emulate anatomical joint loading characteristics. The difficulty in implanting the revision prosthesis along the primary axis is generally attributable to bone loss on the posterior proximal portion of the femur. For example, if a revision femoral component having a symmetric proximal region is to be implanted, the region of proximal bone loss may prevent adequate fixation of the implant in the medullary canal. More particularly, there will be a gap between the implant and the bone which may result in deficient fixation of the femoral component in the proximal region of the femur. To eliminate the gap, a surgeon may attempt a bone graft to replace the lost bone. However, bone grafts can be time consuming and may not ultimately be successful.

Alternatively, a surgeon may implant a revision component that is larger than the original component so as to make up for the bone loss. However, the medullary canal must be reamed to remove additional material to accommodate the larger implant. Generally, the canal is reamed along an axis that is offset from the primary axis to compensate for the proximal bone loss. The offset results in a tendency for the revision component to twist under load since it is displaced from longitudinal axis of the femur, i.e., the primary axis.

Instead of a significantly larger revision component, a custom implant having a geometry adapted to compensate for the proximal bone loss can be implanted. However, the availability of custom implants may be limited. Furthermore, a large inventory of relatively costly components may need to be maintained.

A further option includes the use of a sleeve on a proximal end of a femoral component. However, conventional sleeves have a center that is offset from the centerline of the medullary canal. The offset center point results in misalignment of the revision femoral component with respect to the primary axis so as to provide less than optimal joint loading characteristics. Such displacement of the revision component from the primary axis results in a tendency of the implant to shift in position.

It would, therefore, be desirable to provide a sleeve for use with a revision prosthetic component that compensates for bone loss such that after implantation a longitudinal axis of the revision prosthetic component is coincident with the primary axis.

SUMMARY OF THE INVENTION

The present invention provides a sleeve component for use with a prosthetic joint component. Although the invention is primarily shown and described in conjunction with a femoral hip stem component, and in particular for a surgical revision thereof, it is understood that the sleeve component is applicable to other types of joint prostheses as well, such as knees, elbows and shoulders.

In one embodiment, the sleeve includes a generally annular body having a bore formed therein and a longitudinal axis. The body has an eccentric outer surface with a symmetrical region and a compensating region for offsetting bone loss and/or anatomical anomalies. In an exemplary embodiment, the sleeve is adapted to be secured to a proximal portion of a revision femoral component. The sleeve compensates for proximal, posterior bone loss in the patient's femur that typically occurs during the time that a primary component was implanted.

The contour of the sleeve outer surface, including the compensating region, can be defined by a variety of parameters including radii, location of the radii, shape, such as circular and elliptical, and degree of surface taper. In an exemplary embodiment, the symmetrical region is defined by a first radius extending from a first point located on a longitudinal axis of the sleeve. The compensating region is defined by a second radius extending from a second point which is displaced from the sleeve longitudinal axis. Alternatively, the symmetrical region is defined by a first radius extending from a first point located on the longitudinal axis and the compensating region is defined by a second radius, which is greater than the first radius, also extending from the first point.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
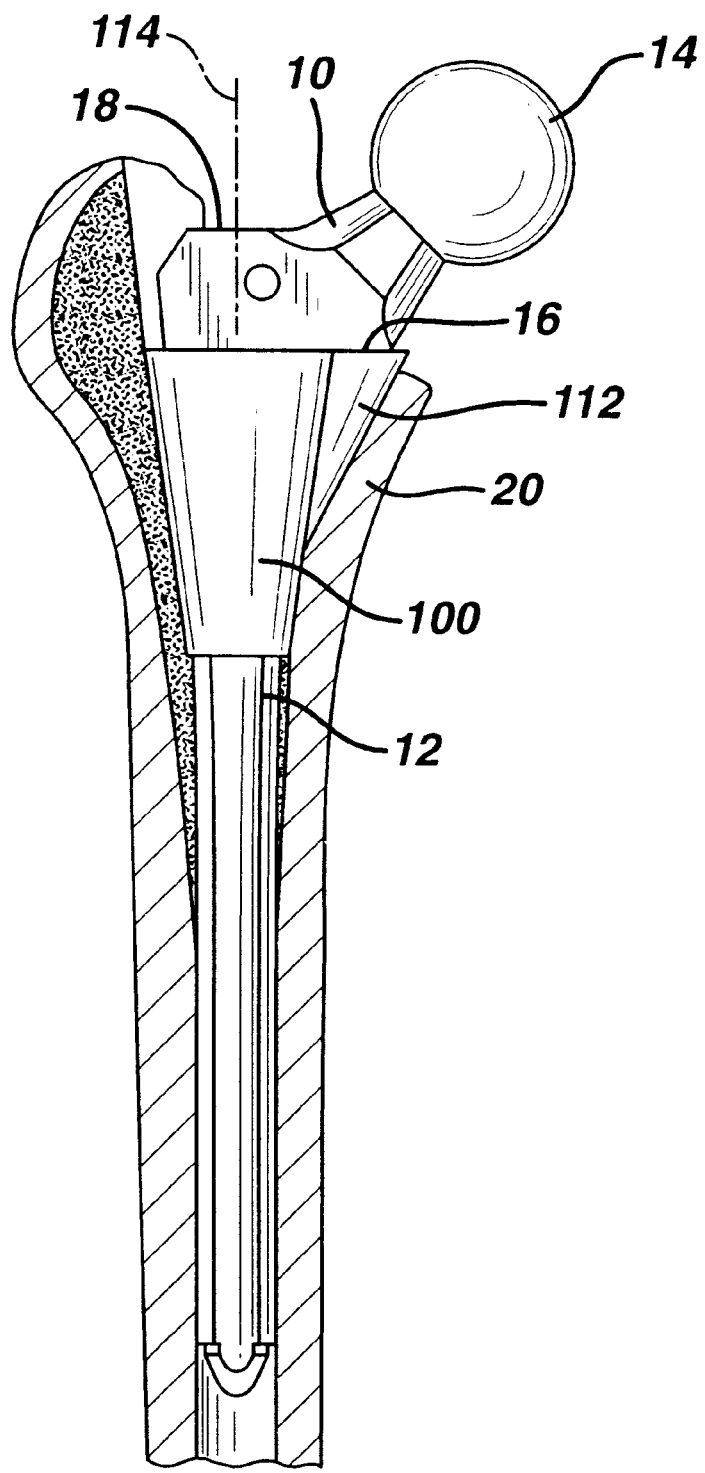
FIG. 1 is a diagrammatic representation of a sleeve, in accordance with the present invention, which is engaged to an implanted femoral component.
Figure 2:
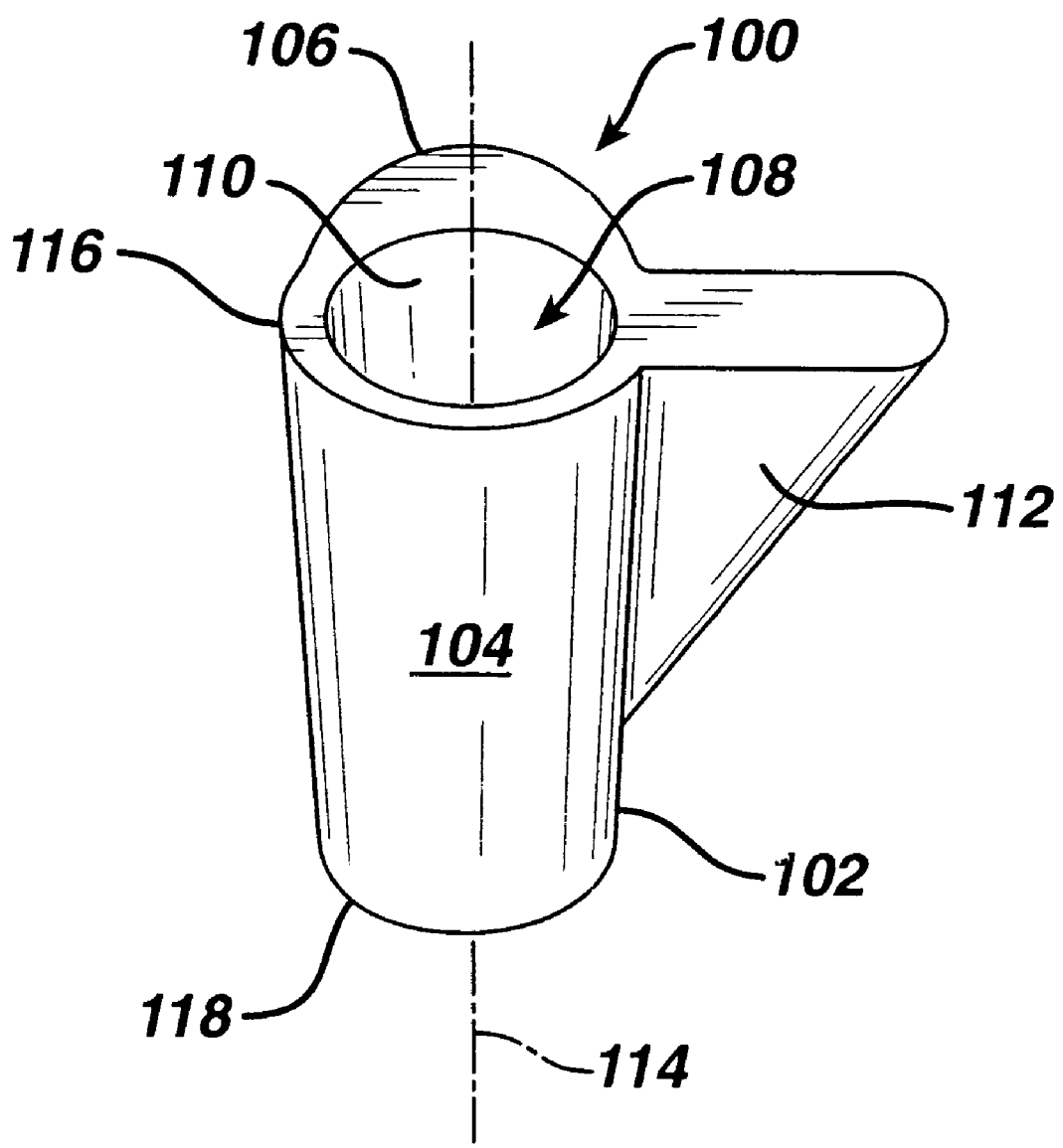
FIG. 2 is a perspective view of the sleeve of FIG. 1.
Figure 3:
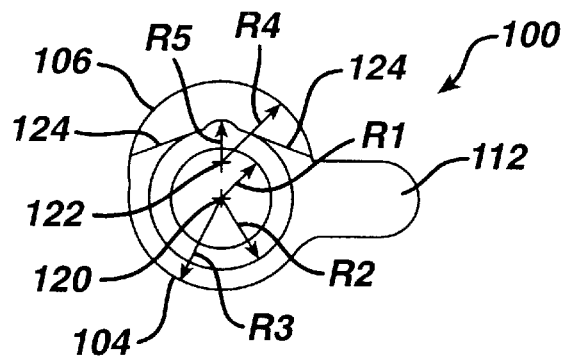
FIG. 3 is a bottom view of the sleeve of FIG. 1.
Figure 4:
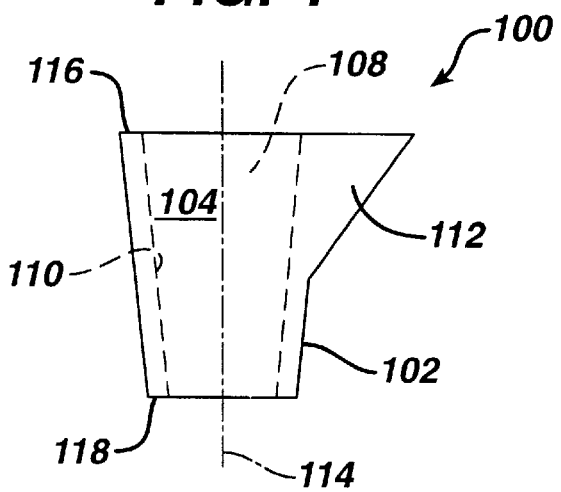
FIG. 4 is a front view of the sleeve of FIG. 3.
Figure 5:
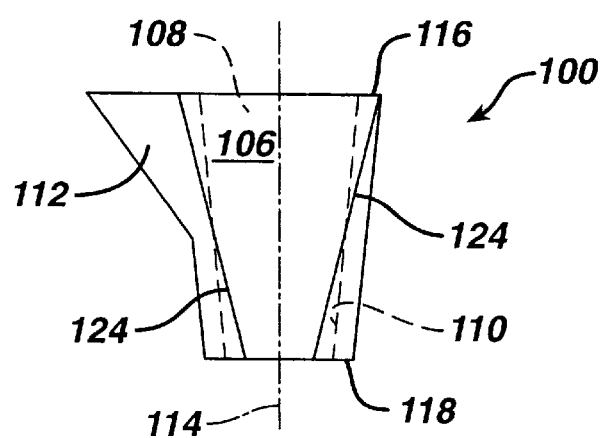
FIG. 5 is a rear view of the sleeve of FIG. 3.
Figure 6:
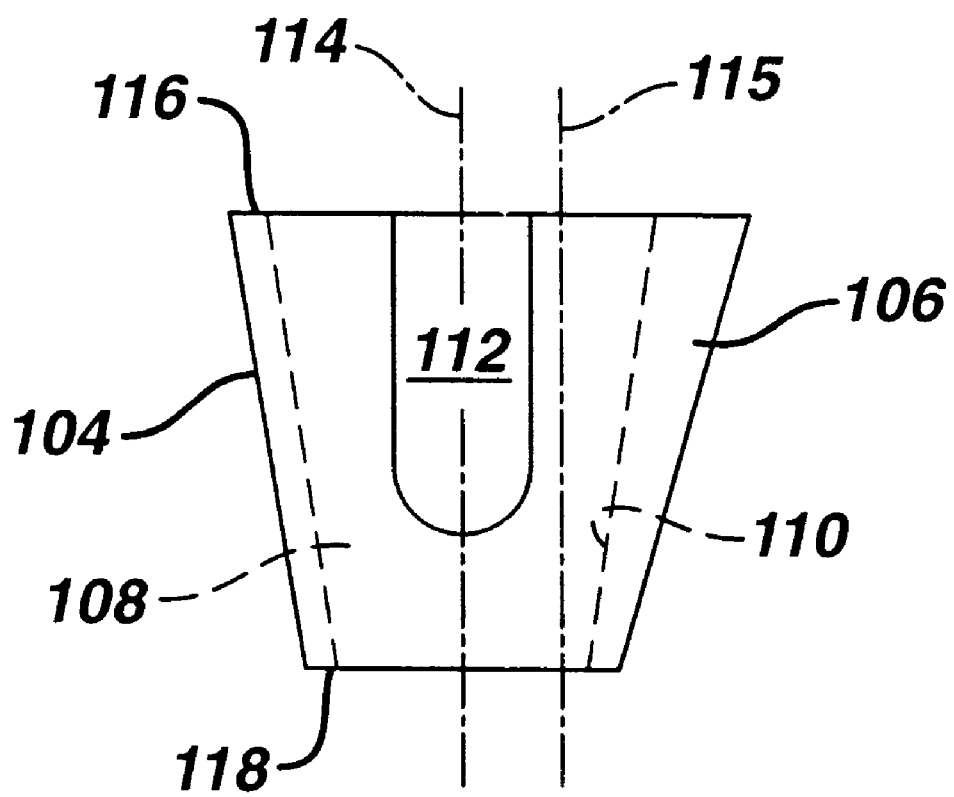
FIG. 6 is a side view of the sleeve of FIG. 3.

FIGS. 1–2 show a sleeve 100 adapted for engagement with an elongate prosthetic component 10, such as a femoral stem, which is implantable within a patient's medullary canal 12. The stem 10 has attached thereto a head or ball 14 for articulating within a natural acetabulum or a prosthetic acetabular component (not shown). The sleeve 100 has a generally tapered, annular body 102 with an outer surface defined by a symmetrical region 104 and a compensating region 106 for offsetting proximal, posterior bone loss in the femur. The compensating region 106 of the sleeve allows a revision femoral component to be implanted along substantially the same axis, i.e., primary axis, as the primary femoral implant while still compensating for proximal bone loss. By implanting the revision prosthetic component along the same axis as the primary implant, the original and anatomical load transfer characteristics are advantageously retained for optimal long term fixation properties.

In general, the sleeve body 102 has a bore 108 formed therein which defines an inner surface 110 with a taper which matches a tapered outer surface of the femoral component 10. The sleeve 100 slides along the femoral stem 10 until the sleeve abuts a shoulder 16 formed on the proximal end 18 of the femoral component. The sleeve 100 can be secured in position on the femoral stem 10 using a variety of techniques including mechanical bonding, frictional engagement, and interlocking surface features. In one embodiment, the sleeve is fixed in position by means of a porous coating covering at least a portion of the sleeve outer surface for promoting bone ingrowth.

The sleeve 100 includes a spout or protruding portion 112 extending from the body 102 for abutting the shoulder 16 of the femoral component. The protruding portion 112 forms an acute angle with the longitudinal axis 114 of the sleeve. The protruding portion 112 is adapted to be seated within the caller region 20 (FIG. 1) of the femur.

The outer surface of the sleeve body 102 can be formed in a variety of geometries to achieve a desired contour to compensate for bone loss in the femur. The symmetrical and compensating regions 104,106 are generally arcuate and may be defined by one or more radii. It is understood that the symmetrical region 104 is generally symmetrical for ease of reaming, but it may be non-symmetrical. That is, it is easier for a surgeon to ream the medullary canal in a symmetrical, e.g., cylindrical, shape. Exemplary shapes for the symmetrical and compensating regions 104,106 include round, elliptical and oblong. Further, the symmetrical and compensating regions 104,106 generally taper such that a proximal end 116 of the sleeve is larger than a distal end 118. Also, the compensating region 106 may extend for the entire length of the sleeve, or only a portion thereof. It is understood that the sleeve outer surface can include surface features formed thereon for promoting fixation and bony ingrowth with surrounding bone.

FIGS. 3–6 in combination with FIGS. 1–2 show further details of the sleeve 100. As shown from the bottom or distal end 118 (see FIG. 3), the bore 108 extends through the sleeve body. The distal end 116 of the bore inner surface 110 is defined by a first radius R1 extending from a first point 120 which is disposed on the longitudinal axis 114 of the sleeve. A second radius R2, which also extends from the first point 120, defines a distal end of the symmetrical region 104 of the sleeve outer surface. A third radius R3, which extends from the longitudinal axis 114 at a proximal end 116 of the sleeve, defines the proximal end of the symmetrical region 104. The symmetrical region 104 tapers from the proximal end 116 to the distal end 118 of the sleeve. It is understood that a first plurality of radii, each of which extends from the longitudinal axis 114, defines the tapered symmetrical region 106 between the proximal and distal ends 116,118 of the sleeve. The first plurality of radii includes the second and third radii R2,R3.

The compensating region 106 of the sleeve is defined at the top or proximal end 116 by a fourth radius R4 extending from a second point 122 which is offset from the first point 120. The second point 122 is located on an axis 115 (FIG. 6) which is offset from the longitudinal axis 114. The distal end of the compensating region 106 is defined by a fifth radius R5 which extends from the offset axis 115 at the distal end 118 of the sleeve. The compensating region 106 generally tapers from the proximal end 116 to the distal end 118 in a manner similar to the symmetrical region 104 so as to form a boundary 124 between the two regions 104,106. It is understood that a second plurality of radii, each of which extends from the offset axis 115, define the compensating region 106. The second plurality of radii includes the fourth and fifth radii R4,R5. The offset axis can be substantially parallel to or it can be slightly angled with respect to the longitudinal axis 114 of the sleeve.

Figure 7:
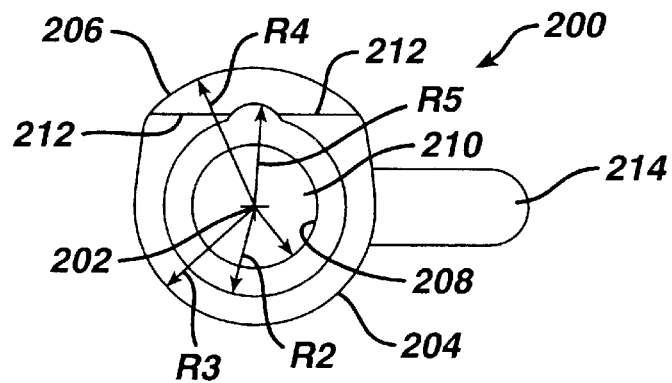
FIG. 7 is a bottom view of another embodiment of a sleeve in accordance with the present invention.
Figure 8:
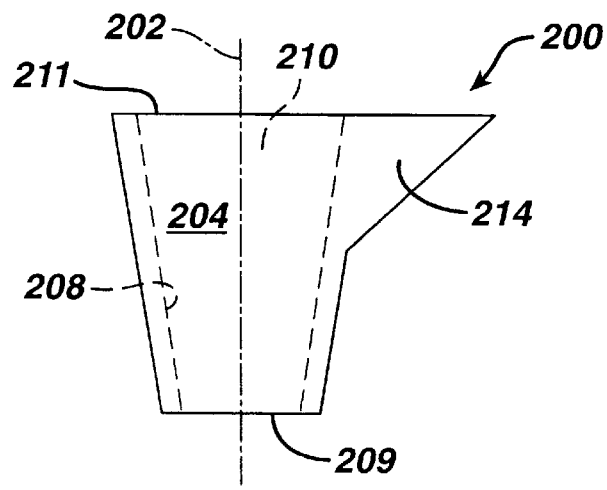
FIG. 8 is a front view of the sleeve of FIG. 7.
Figure 9:
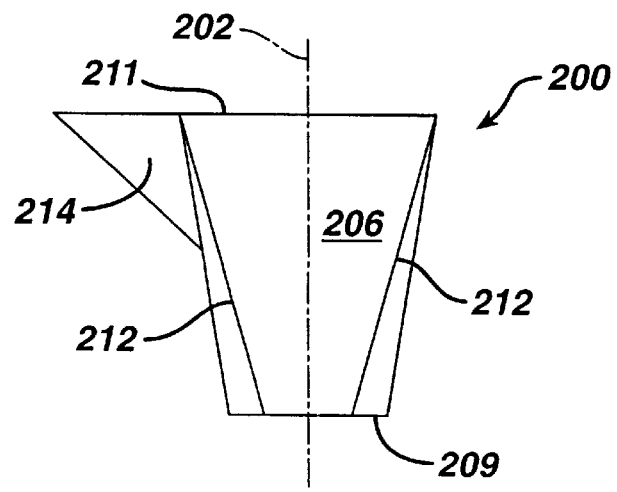
FIG. 9 is a rear view of the sleeve of FIG. 7.

FIGS. 7–9 show a sleeve 200 having an outer surface defined by multiple radii extending from a longitudinal axis 202 with the symmetrical and compensating regions 204, 206 being defined by the length of the respective radii. As shown in the bottom view of FIG. 7, the inner surface 208 of a distal end 209 of the bore 210 is defined by a first radius Ri and the distal end of the symmetrical region 204 is defined by a second radius R2. A third radius R3, which is greater than the second radius R2, defines the larger proximal end 211 of the symmetrical region 204 of the sleeve. The third radius R3 extends from the longitudinal axis 202 at the proximal end 211 of the sleeve.

A fourth radius R4 defines the proximal end 211 of the compensating region 206 and a fifth radius R5 defines a distal end 209 of the compensating region 206. A boundary 212 apportions the compensating region 206 and the symmetrical region 204 of the sleeve outer surface. The increased length of the fourth radius R4, as compared with the length of the third radius R3, and the increased length of the fifth radius R5, as compared with the length of the second radius R2, combine to provide the eccentric geometry of the sleeve outer surface.

The sleeve 200 may also include a spout or protruding region 214 for abutting a shoulder region of a femoral component.

Figure 10:
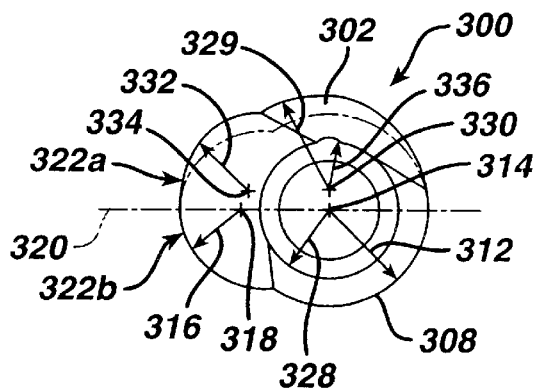
FIG. 10 is a bottom view of a further embodiment of a sleeve in accordance with the present invention.
Figure 13:
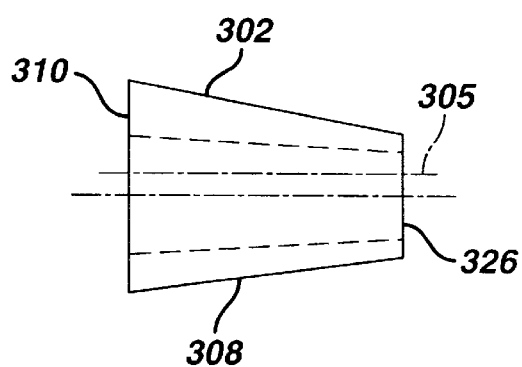
FIG. 13 is side view of the sleeve of FIG. 10.
Figure 11:
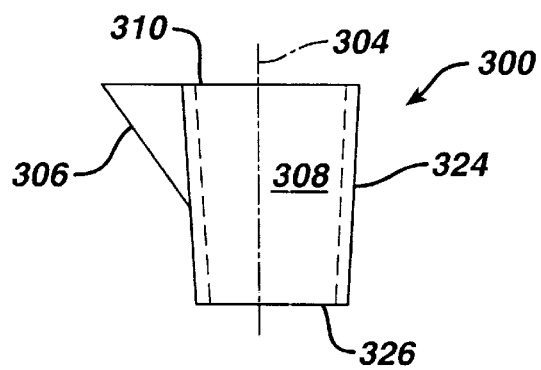
FIG. 11 is a front view of the sleeve of FIG. 10.
Figure 12:
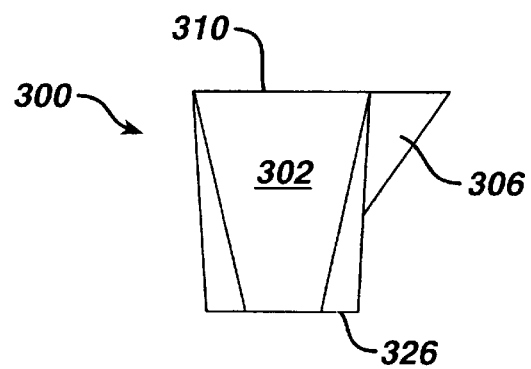
FIG. 12 is a rear view of the sleeve of FIG. 10.
Figure 14:
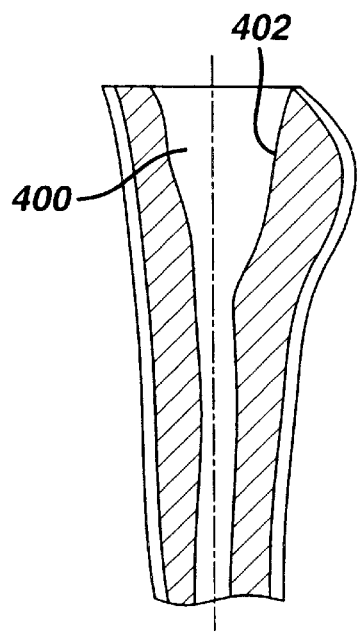
FIG. 14 is a prior art diagrammatic illustration of a medullary canal after removal of a primary femoral component.
Figure 15:
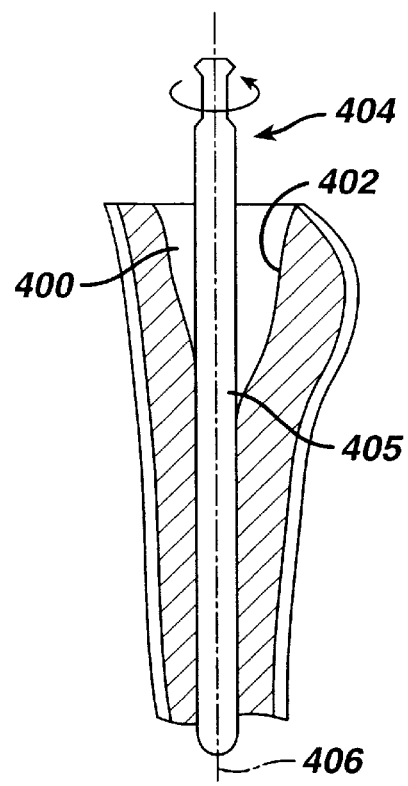
FIG. 15 is a prior art diagrammatic illustration of the medullary canal of FIG. 14 being reamed.
Figure 16:
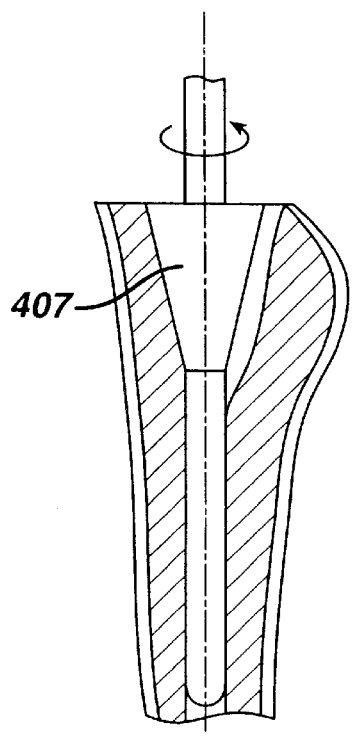
FIG. 16 is a prior art diagrammatic illustration of a proximal region of the medullary canal of FIG. 15 being reamed.
Figure 17:
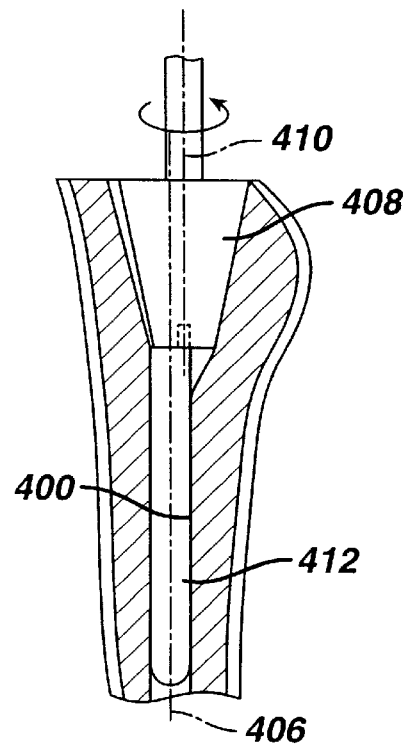
FIG. 17 is a diagrammatic illustration of a reaming instrument for reaming the medullary canal to receive a sleeve in accordance with the present invention.

FIGS. 10–13 show a further embodiment of a sleeve 300 in accordance with the present invention. The sleeve 300 has a compensating region 302 defined by multiple radii which extend from corresponding axes. The sleeve 300 includes a protruding portion 306 which defines a part of the compensating region 302 and a part of a symmetrical region 308. FIG. 10 shows in phantom an extension of the symmetrical region 308 into the compensating region 308 to emphasize the differences in shape between the two regions.

As shown in the bottom view of FIG. 10, a proximal end 310 of the symmetrical region 302 is defined by a first radius 312 extending from a first point 314 located on the longitudinal axis 304 of the sleeve and a second radius 316 extending from a second point 318 which is located a predetermined distance from the longitudinal axis 304. It is understood that the first and second points 314,318 are generally coplanar with the proximal end 310 of the sleeve. In an exemplary embodiment, the first and second points 314,318 are located on a first plane 320 which divides the sleeve into first and second portions 322a, 322b. The first radius 312 defines an area of the symmetrical region 308 corresponding to the sleeve body 324 and the second radius 316 defines an area of the symmetrical region corresponding to the protruding portion 306 of the sleeve.

The distal end of 326 the symmetrical region 308 is defined by a third radius 328 which extends from the longitudinal axis 304 at the distal end of the sleeve. As shown, the sleeve tapers from the proximal end 310 to the distal end 326.

The proximal end 310 of the compensating region 302 is provided in part by the body 324 of the sleeve and in part by the protruding portion 306. A fourth radius 329 extends from a third point 330 which is located on an axis 305 that is offset from the longitudinal axis 304. The third point 330 is disposed at the proximal end 310 of the sleeve. The fourth radius 329 defines a proximal area of the compensating region 302 that corresponds to the sleeve body 324. A fifth radius 332 extends from a fourth point 334 which is offset from the second point 318 to define an area of the compensating region 302 that corresponds to the protruding portion 306 of the sleeve.

The distal end 326 of the compensating region 302 is provided by the sleeve body 324 alone since the protruding portion 306 extends for only a portion of the sleeve. A sixth radius 336 extending from the offset axis 305 at the sleeve distal end 326 defines the distal-most perimeter of the compensating region 302.

The overall dimensions and respective radii for the disclosed embodiments can vary to achieve a desired geometry for the sleeve. An exemplary offset distance from the first point 120 to the second point 122 (FIG. 3) can vary from about two millimeters to about ten millimeters. The length of the radii can vary to compensate for bone loss as determined by visual and/or X-ray imaging techniques, for example. The fourth radius R4 has an exemplary length in the range from about five millimeters to about twelve millimeters and the fifth radius R5 has a length in the range from about three millimeters to about twelve millimeters. In general, greater offset distances are inversely proportional to radial lengths for radii which define the compensating region of the sleeve outer surface.

It is understood that, in view of the embodiments described herein, one of ordinary skill in the art can readily modify the lengths of the radii which define the sleeve, as well the points from which the radii extend, either singly or in combination, to achieve a particular geometry for the sleeve outer surface.

The sleeves described above are well suited for use with a revision femoral component to compensate for proximal, posterior bone loss that occurs during the time that the primary femoral component remains implanted in the patient's femur.

In an exemplary technique to use a sleeve in accordance with the present invention to compensate for bone loss, the surgeon first removes the primary component using methods well known to one of ordinary skill in the art. The medullary canal is then reamed to prepare it for receiving a revision femoral component. In general, the size of the canal must be expanded to remove any bone cement and bony ingrowth areas. In contrast to using conventional sleeve components, a femoral component/sleeve assembly as described herein is implanted along the primary axis. That is, the canal is reamed to the extent necessary along the same axis as for the primary or original implant, which typically corresponds to the longitudinal axis of the bone. This is advantageous because loads on the bone are transferred along this axis. When an implant is offset from the primary axis, loads will tend to twist the implant thereby decreasing the likelihood of long term fixation of the implant in the bone.

FIGS. 14–17 show an exemplary technique and apparatus for creating a cavity in the bone to receive a femoral component/sleeve assembly in accordance with the present invention. A primary femoral component (not shown) is first removed to expose the medullary canal 400 of a bone (FIG. 14) A posterior/proximal region 402 of the medullary canal exhibits bone loss, as shown. A conventional reaming device 404 (FIG. 15) having a cylindrical reamer 405 is used to ream the canal 400 along a longitudinal or primary axis 406 of the bone in preparation for implantation of a revision femoral stem. As shown, the conventional reamer 404 does not remove bone in the posterior/proximal region 402 of the medullary canal. A frustoconical reamer 407 is used to ream a symmetrical cavity about the primary axis 406 in a proximal region of the medullary canal 400. The calcar region 20 (FIG. 1) of the femur is reamed to complement the spout or protruding portion 112 of the sleeve 100 (FIG. 1), which abuts the shoulder 16 of the stem 10. The cavity for the protruding portion 112 of the sleeve can be reamed as shown and described in U.S. Pat. No. 4,790,852, to Noiles, which is incorporated herein by reference.

The proximal region 402 of the medullary canal must be reamed such that it conforms to the outer surface of the sleeve 100 (FIGS. 1–2). That is, the canal 400 must be reamed to complement the eccentric outer surface of the sleeve, e.g., the compensating region 106. Triangular and/or conical reamers, for example, can be used to achieve the necessary eccentric reaming of the canal. In one embodiment, a frustoconical reamer 408 (FIG. 17) aligned with an offset axis 410 using a cylindrical guide 412 which is inserted into the medullary canal 400. This arrangement reams the proximal/posterior region of the medullary canal such that it matches the symmetrical and compensating regions 104,106 (FIG. 2) of the sleeve 102 outer surface.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A sleeve for engagement with a prosthetic component which is implantable within a medullary canal in a patient, the sleeve comprising:

an elongate body having a bore formed therein through which a prosthetic component is insertable, the body including a symmetrical surface region, a spout, and an eccentric outer surface having a compensating region that extends outwardly proximate to a region of bone loss for compensating for bone loss.

2. The sleeve according to claim 1, wherein the symmetrical region is defined by a first range of radii extending from a first point.

3. The sleeve according to claim 2, wherein the compensating region is defined by a second range of radii extending from a second point.

4. The sleeve according to claim 3, wherein the second point is offset from the first point.

5. The sleeve according to claim 4, wherein the first point is located on a longitudinal axis of the sleeve.

6. The spout according to claim 1, wherein the spout includes a protruding region distinct from the compensating region and the symmetrical region for abutting a shoulder of the prosthetic component.

7. The sleeve according to claim 1, wherein the body is tapered.

8. The sleeve according to claim 3, wherein the first point is aligned with the second point.

9. The sleeve according to claim 8, wherein a first one of the first plurality of radii is less than a corresponding first one of the second plurality of radii.

10. The sleeve according to claim 1, wherein the compensating region extends along the entire length of the sleeve.

11. A sleeve for coupling to a proximal end of a femoral component, comprising:
a body having a longitudinal axis and first and second ends with a bore extending therebetween, the body having a symmetrical outer surface region, and spout and an eccentric outer surface with a compensating region that extends outwardly proximate to a region of bone loss for compensating for proximal posterior bone loss in a patient's femur,
the symmetrical region being defined by a first range of radii extending from the longitudinal axis and
the compensating region being defined by a second range of radii extending from an axis which is offset from the longitudinal axis.

12. The sleeve according to claim 11, wherein the offset between the longitudinal axis and the offset axis ranges from about two millimeters to about ten millimeters.

13. The sleeve according to claim 11, wherein the body is tapered.

14. The sleeve according to claim 11, wherein the body has a thickness that varies in the compensating region.

15. A sleeve for coupling to a proximal end of a femoral component, such sleeve comprising:
a body having a longitudinal axis and first and second ends with a bore extending therebetween, the body having a symmetrical outer surface region and an eccentric outer surface with a compensating region that extends outwardly proximate to a region of bone loss for compensating for proximal posterior bone loss in a patient's femur, the symmetrical region being defined by a first plurality of radii extending from a first point located on the longitudinal axis and the compensating region being defined by a second plurality of radii extending from the longitudinal axis, wherein a first one of the first plurality of radii is less than a corresponding first one of the second plurality of radii such that at the first end of the body the compensating region has a thickness greater than that of the symmetrical region.

16. The sleeve according to claim 15, wherein the sleeve is tapered.

17. The sleeve according to claim 15, wherein the compensating region extends along an entire length of the sleeve.

18. A sleeve for coupling to a femoral stem, comprising:
a generally cylindrical body having a longitudinal axis and a protruding portion extending from the body toward a region of bone loss, the body having an eccentric outer surface formed by a symmetrical region and a compensating region for compensating for bone loss in a proximal, posterior region of a patient's femur, the compensating region having a first portion corresponding to the cylindrical body and a second portion corresponding to the protruding portion.

19. The sleeve according to claim 18, wherein the first portion of the compensating region is defined by radii extending from a first axis which is offset from the longitudinal axis.

20. The sleeve according to claim 19, wherein the second portion of the compensating region is defined by radii extending from a second axis which is offset from the longitudinal axis.

21. A reaming device for reaming an eccentric cavity in a medullary canal of a bone that has a longitudinal axis, comprising:
a rotating member having a proximal end and a distal end, the rotating member being rotatable about an offset axis which is offset from the longitudinal axis of the bone;
a reamer having a frustoconical outer surface coupled to the rotating member, the reamer being rotatable about the offset axis; and
a guide member for being inserted into the medullary canal in alignment with the bone's longitudinal axis,
wherein the reamer forms an eccentric cavity for complementing an outer surface of a tapered sleeve component having an eccentric outer surface with a compensating region for compensating for bone loss, wherein the compensating region includes a symmetrical region and a region that extends outwardly proximate to a region of bone loss.

* * * * *